(12) United States Patent
Analytis et al.

(10) Patent No.: US 11,298,445 B2
(45) Date of Patent: Apr. 12, 2022

(54) BREAST PUMP MILK FLOW RATE SENSOR SYSTEM AND APPARATUS

(71) Applicant: Moxxly LLC, Wilmington, DE (US)

(72) Inventors: Santhi Analytis, San Francisco, CA (US); Wisit Jirattigalachote, San Francisco, CA (US); Jacob Kurzrock, San Francisco, CA (US)

(73) Assignee: Moxxly, LLC, Wilmington, DE (US)

( * ) Notice: Subject to any disclaimer, the term of this patent is extended or adjusted under 35 U.S.C. 154(b) by 423 days.

(21) Appl. No.: 16/243,996

(22) Filed: Jan. 9, 2019

(65) Prior Publication Data

US 2019/0209747 A1 Jul. 11, 2019

Related U.S. Application Data

(60) Provisional application No. 62/615,147, filed on Jan. 9, 2018.

(51) Int. Cl.
*A61M 1/06* (2006.01)
*A61M 39/22* (2006.01)

(52) U.S. Cl.
CPC .............. *A61M 1/062* (2014.02); *A61M 1/06* (2013.01); *A61M 39/22* (2013.01); *A61M 2205/3306* (2013.01); *A61M 2205/3334* (2013.01); *A61M 2205/3576* (2013.01)

(58) Field of Classification Search
CPC ........ A61M 1/06; A61M 1/062; A61M 1/064; A61M 1/066; A61M 1/068; A61M 1/0072; A01J 5/01; A01J 5/007; A01J 5/041; A61J 9/00
See application file for complete search history.

(56) References Cited

U.S. PATENT DOCUMENTS

| | | | | | |
|---|---|---|---|---|---|
| 3,217,709 | A | * | 11/1965 | Schneider | A61M 5/1411 604/251 |
| 3,390,577 | A | * | 7/1968 | Phelps | A61M 5/1689 73/861.41 |
| 6,663,587 | B2 | * | 12/2003 | Silver | A61M 1/064 119/14.47 |
| 9,623,160 | B2 | * | 4/2017 | Alvarez | A61M 1/06 |
| 10,796,797 | B2 | * | 10/2020 | Guthrie | G06F 3/04847 |

* cited by examiner

*Primary Examiner* — Manuel A Mendez
(74) *Attorney, Agent, or Firm* — Loyal Intellectual Property Law, PLLC; Travis Banta

(57) ABSTRACT

A breast pump milk flow rate sensor system and apparatus for accurately assessing both a flow rate and amount of milk expressed during a pumping session is provided. The breast pump milk flow rate sensor system and apparatus may be contained within a breast pump.

19 Claims, 6 Drawing Sheets

BREAST PUMP MILK FLOW RATE SENSOR SYSTEM AND APPARATUS

CROSS-REFERENCE TO RELATED APPLICATIONS

This application claims the benefit of U.S. Provisional Patent Application Ser. No. 62/615,147, filed Jan. 9, 2018, entitled "BREAST PUMP MILK FLOW RATE SENSOR SYSTEM AND APPARATUS," which is incorporated herein by reference in its entirety, including but not limited to those portions that specifically appear hereinafter, the incorporation by reference being made with the following exception: In the event that any portion of the above-referenced application is inconsistent with this application, this application supercedes said portion of said above-referenced application.

BACKGROUND

1. Technical Field

This disclosure relates generally to a breast pump for nursing mothers. More specifically, the devices and systems disclosed herein relate to a milk flow rate sensor system and apparatus for accurately assessing both a flow rate and amount of milk expressed during a pumping session.

2. Description of the Related Art

Nursing an infant can be an emotional experience for many nursing mothers. While nursing can be profoundly rewarding for a new mother, many mothers have difficulty nursing a new baby. Breast pumps have been developed to help women express milk by mechanical systems to feed to their babies. To that end, breast pumps have been developed to not only assist mothers who experience difficulty in nursing infants, but also to allow mothers who are away from their babies provide milk for their infants to drink at another time and help many mothers maintain and develop their milk supply.

Conventional breast pump systems are not well suited for today's user. These breast pumps offer only simple information about milk that has been pumped by, for example, including fluidic measurement gradations on the sides of a milk catchment bottle. By comparing the level of milk in the milk catchment bottle against the fluidic measurement gradations on the sides of the milk catchment bottle, a mother can assess that perhaps some amount of milk between two ounces and two and a half ounces, for example, were expressed during a particular pumping session. Such measurements serve only to approximate the amount of milk expressed during a particular pumping session.

Fluidic measurement gradations, while helpful for approximation, can be less than accurate. For example, if a milk catchment bottle is not absolutely flat, the level of milk within the bottle can be higher on one side than on another. Depending on which side of the bottle is marked with the fluidic measurement gradations, milk within the bottle being higher on one side than another can lead a mother to believe more or less milk has been produced than actually has been. This situation is worsened when the milk is inside a deformable container such as a freezer bag.

Another issue with using fluidic measurement gradations is that the amount of milk expressed is based on a per-breast expression. In many cases, mothers pump milk from each breast simultaneously. As a result, milk is caught in two separate milk catchment bottles, each of which are individually marked with fluidic measurement gradations. Thus, one milk catchment bottle may contain a two and five eighths of an ounce of milk while a second milk catchment bottle may contain three and one third of an ounce of milk. Because fractional amounts of milk may be difficult to add together, many mothers pour the milk from both bottles into a single bottle with another series of fluidic measurement gradations to re-compare the level of milk in the bottle to the fluidic measurement gradations to get an approximate measurement of the amount of milk expressed during that particular pumping session. In another alternative assessment, a mother may pour milk from one milk catchment into the other milk catchment bottle to a certain gradation level to make the mathematical addition of fluidic measurements easier.

Both alternatives, however, present certain problems. First, pouring milk back and forth from one milk catchment bottle to another increases the likelihood that some milk will be spilled and thus lost. Second, introducing a third bottle merely for measuring the amount of milk that has been expressed during a pumping session increases the number of parts, bottles, and other pieces that must be re-sterilized. Third, in either alternative, the amount of milk expressed is still mostly approximated by the fluidic measurement gradations on the side of the milk catchment bottle and are subject to inherent inaccuracies based on the bottle leaning more to one side than another during measurement. And, finally, mathematical errors may result in a mother thinking her baby ate more when in fact the baby ate less than the mother incorrectly calculated or vice versa.

It is therefore one object of this disclosure to provide a milk flow rate sensor system and apparatus. An additional object is to provide a system to track flow rate and volume of expressed milk in each breast separately, and/or cumulatively. It is a further object of this disclosure to provide an apparatus that portions milk into uniform droplets. Another object of this disclosure is to provide a sensor to sense uniform milk droplets over time to provide a fluidic measurement and/or a flow rate of the amount of milk expressed.

SUMMARY

Disclosed herein is a breast pump including a manifold. The breast pump further includes a drain connected to the manifold. The drain includes a droplet forming spout. The sensor is disposed under the droplet forming spout in the breast pump. The sensor detects droplets of milk released from the spout.

Further disclosed is a breast pump that includes a drain apparatus. The drain apparatus includes a droplet forming spout. The breast pump further includes a sensor. The sensor is disposed under the droplet forming spout. The sensor detects droplets of milk released from the spout.

BRIEF DESCRIPTION OF THE DRAWINGS

The accompanying drawings illustrate one or more embodiments of a breast pump implementing a milk flow rate sensor system and apparatus for accurately assessing both a flow rate and amount of milk expressed during a pumping session.

DETAILED DESCRIPTION OF PREFERRED EMBODIMENTS

In the following description, for purposes of explanation and not limitation, specific techniques and embodiments are set forth, such as particular techniques and configurations, in order to provide a thorough understanding of the device disclosed herein. While the techniques and embodiments will primarily be described in context with the accompanying drawings, those skilled in the art will further appreciate that the techniques and embodiments may also be practiced in other similar devices.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to particular embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Figure 1:
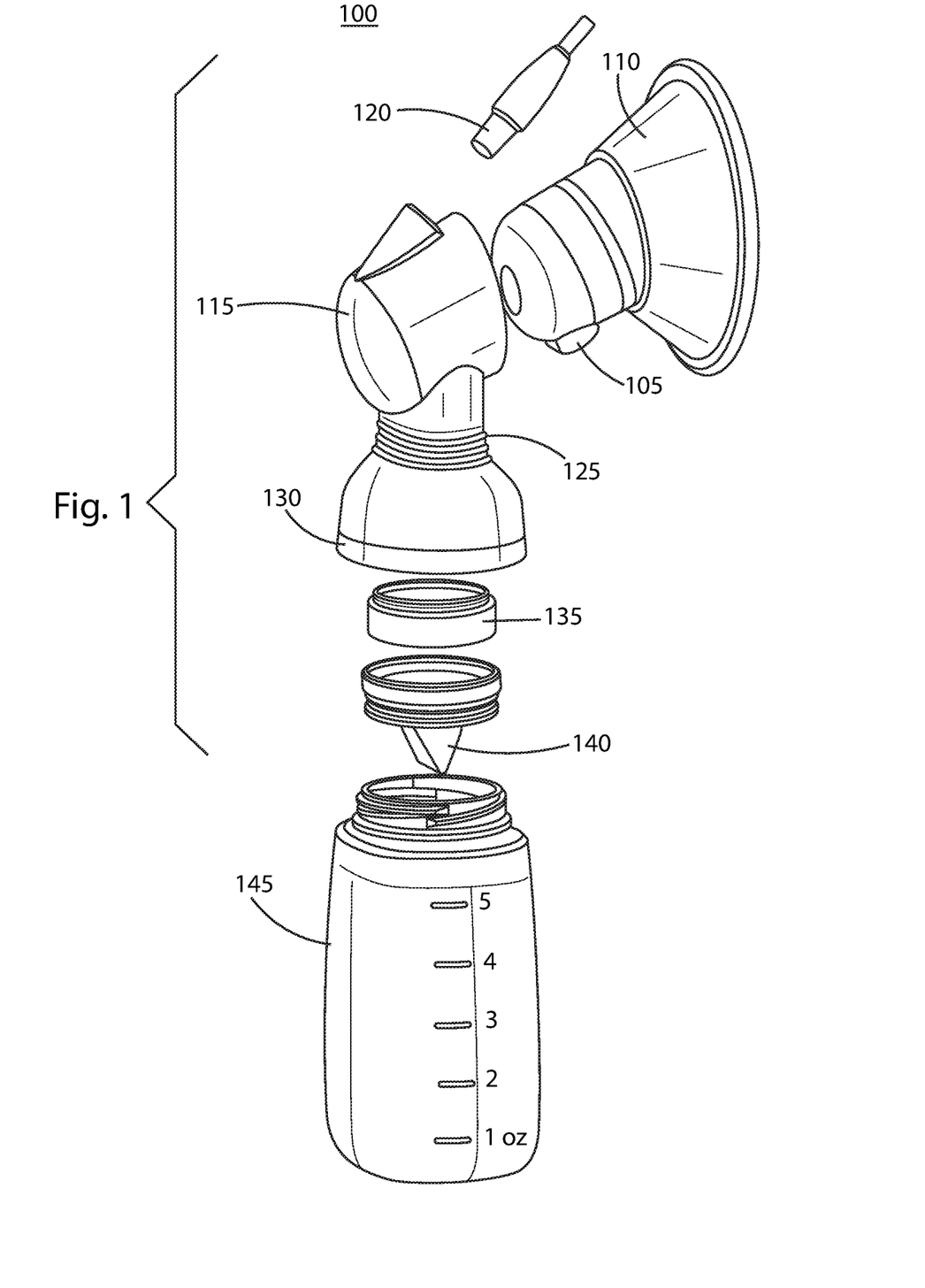
FIG. 1 illustrates a breast pump implementing a milk flow rate sensor system and apparatus.

FIG. 1 illustrates a breast pump 100. Breast pump 100 includes a flange 105, which includes a support cone 110 or a rigid region around the areola, which connects to manifold 115 using an airtight tapered friction fitting. Flange 105 may connect to manifold 115 via a tapered friction fitting or mechanical threads or snaps or retaining rings. In one embodiment, flange 105 may provide a user with tactile feedback with a step on support cone 110 to meet the manifold 115 in a manner that helps the user correctly align the flange 105 with manifold 115. In another embodiment, a flow sensor, which will be discussed herein, may be disposed between flange 105 and manifold 115. Manifold 115 may house a number of elements, which are not shown in FIG. 1, including computer hardware, one or more processors, various types of memory (static, dynamic, flash, etc), receivers, transmitters, antennas, various sensors, a vacuum pump, and other elements that make breast pump 100 capable of interacting with, for example, a mobile device, such as a mobile phone. A vacuum pump, not shown, may also be a component that is external to breast pump 100 and may connect to breast pump 100 via tubing adapter 120 attached to manifold 115. Tubing adapter 120 connects pneumatic tubing (not shown) to manifold 115 and may also provide tactile feedback to the user to ensure that tubing adapter 120 is properly connected to manifold 115. Tactile feedback may be provided by a series of mechanical stops installed in the various elements of breast pump 100 that provide the user a sense that the elements of breast pump 100 are correctly assembled. These feedback points may be used to turn a sensor ON only when correctly assembled. In order to enhance the comfort of breast pump 100, manifold 115 includes a flexible neck 125 which may remain flexible or may be flexed into a particular position and held there by flexible neck 125. A sensor may be housed at, above, or below a portion of the flexible neck.

Manifold 115 includes a manifold base 130 which connects to milk flow rate sensor system and apparatus 135. In general, milk flow rate sensor system and apparatus 135 receives milk as it drains through manifold 115 into milk flow rate sensor system and apparatus. Milk flow rate sensor system and apparatus 135 serves to remove air bubbles from milk collected within the milk flow rate sensor system and apparatus and to create uniform milk droplets. The droplets pass through a spout that ensures each droplet contains substantially the same amount of milk. The droplets fall from milk flow rate sensor system and apparatus 135 into an associated sensor which counts the droplets as they pass through a sensor region associated with milk flow rate sensor system and apparatus 135. The associated sensor may provide information to one or more computer processors which may use adaptable volume multipliers when milk flow is detected to be passing the sensor in drops or in streams. For example, when the associated sensor detects drops, a higher volume multiplier may be applied by the processor to determine a volume of expressed milk. Similarly, and for example, when the associated sensor detects a stream of milk, a lower volume multiplier may be applied by the processor to determine a volume of expressed milk. More simply put, the volume multiplier used to determine a volume of expressed milk may adjustable and adaptable based on flow rate. One or more processors for collecting sensor data may be implemented in one or both of manifold 115 or apparatus 135, a milk collection apparatus 145, or in a connected mobile device (e.g., a smart phone or a tablet wirelessly connected and configured to receive sensor data via one or more processors. Alternatively, the sensor portion can use liquid level sensing, capacitive sensing or weight-based measurements without the need to remove bubbles or control drops. Milk flow rate sensor system and apparatus 135 will be discussed in more detail, below. Sensor data from any sensor disclosed herein may be provided from breast pump 100 to a mobile device, including calculated flow rate and volume information. If two breast pumps 100 are used simultaneously, sensor data from both breast pumps 100 may be sent to the mobile device which may provide updated corresponding information (summation of information from both breast pumps 100).

Breast pump 100 further includes a connector (not shown) that connects to a milk collection apparatus 145 which houses valve 140. In one embodiment, the connector in manifold base 130 may include female threads to receive male threads on milk collection apparatus 145. Alternatively, manifold base 130 may include a friction connector, which allows milk collection apparatus 145 to "snap" into manifold base 130. In a further embodiment, the connector in manifold base 130 may include a specific thread pattern to allow milk collection apparatus 145 to be fully secured by a quarter turn connection. More specifically, the connector in manifold base 130 may allow milk collection apparatus 145 to be fully secured to manifold base 130 by threading milk collection apparatus 145 into the connector in manifold base 130 and turning milk collection apparatus 145 90°. The user may be visually and tactilely cued that the parts are correctly assembled by the parts fitting together. In other words, mechanical stops may be installed that "snap" together, or give some other sensation, that assures the user the parts are correctly assembled. These feedback points may be used to turn a sensor ON only when correctly assembled.

In practice, breast pump 100 is applied to a mother's breast by securing support cone 110 to a nipple area of the mother's breast. Vacuum pressure may then be applied by a vacuum pump through tubing 120 connected to manifold 115. As the vacuum pump cycles between an on state and an off state, milk is expressed from the mother's breast. The milk is allowed to drain through support cone 110 into manifold 115 and into milk flow rate sensor system and apparatus 135. Milk flow rate sensor system and apparatus 135 portions droplets into substantially the same volume of milk and senses each drop as it falls into valve 140. Valve 140 allows the milk to selectively drain in to milk collection apparatus 145. Valve 140 includes an opening which allows milk to drain from valve 140 into milk collection apparatus 145. At the same time, however, valve 140 maintains the vacuum created within support cone 110, and manifold 115 by selectively opening and closing in response to vacuum pressure. For example, when vacuum pressure is being applied to a mother's breast, the vacuum pressure forces valve 140 to close and maintain the vacuum. When the vacuum pressure is off, valve 140 opens and allows milk to flow into milk collection apparatus 145. As the duty cycle of the vacuum pump rapidly alternates between application of vacuum pressure to the mother's breast and not applying vacuum pressure to the mother's breast (to simulate a suckling infant), valve 140 selectively responds to maintain vacuum pressure or allow milk to flow into milk collection apparatus 145. The sensor apparatus may reside above or below the valve.

Figure 2:
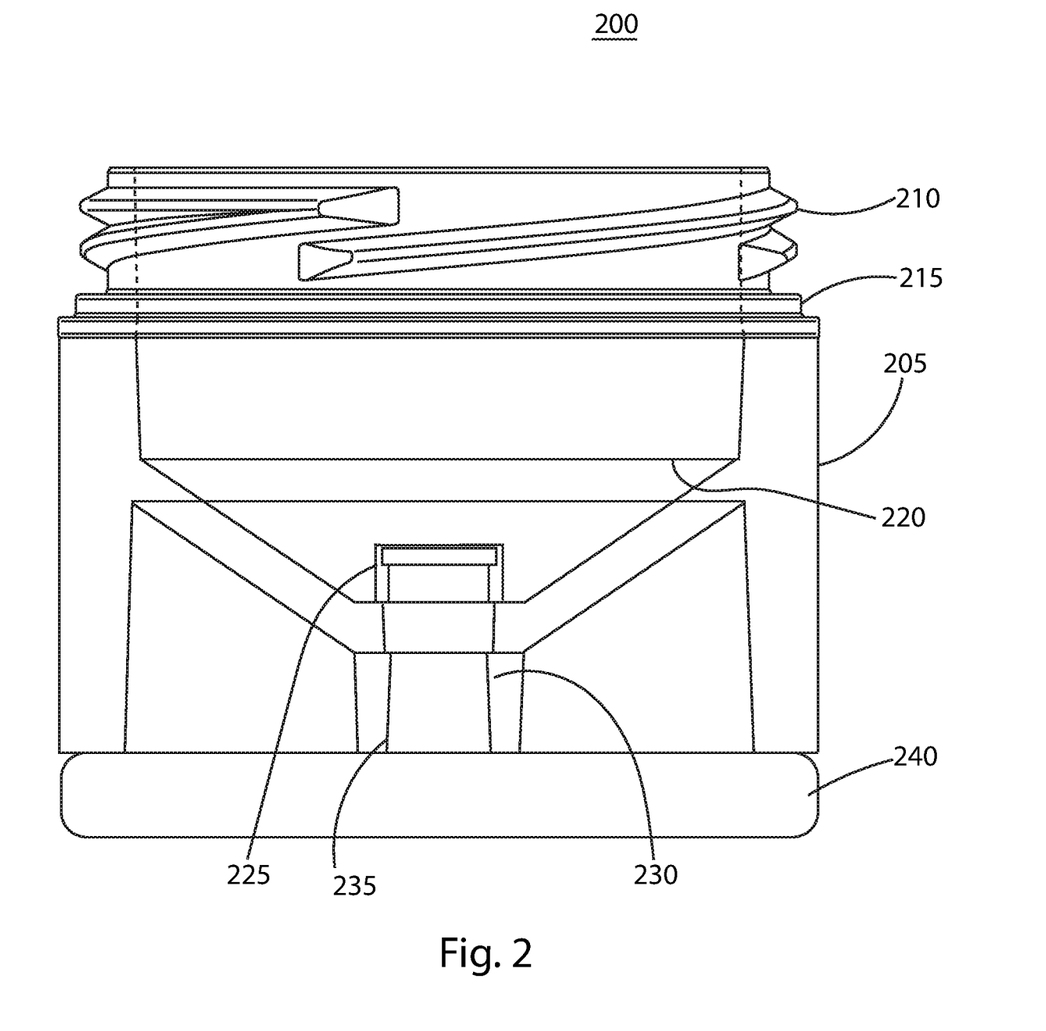
FIG. 2 illustrates a cut-away side view of the milk flow rate sensor system and apparatus.

FIG. 2 illustrates a cut-away side view of the milk flow rate sensor apparatus 200 used with a breast pump, such as breast pump 100 shown and described above with respect to FIG. 1. Milk flow rate sensor apparatus 200 includes a housing 205 which may be constructed using an injection molding process to create a hard plastic apparatus. In one embodiment, milk flow rate sensor apparatus 200 includes a connector 210 to connect milk flow rate sensor apparatus 200 to, for example, manifold base 130 shown in FIG. 1. Connector 210 may include male mechanical threads which may be connected to manifold base 130 by screwing mechanical threads on connector 210 into female threads on manifold base 130. In one embodiment, connector 210 may implement a "quarter turn lock" mechanical thread engagement system. In this embodiment, milk flow rate sensor apparatus 200 may be attached to manifold base 130 by turning milk flow rate sensor apparatus 200 90° into manifold base 130 to form a secure connection between milk flow rate sensor apparatus 200 and manifold base 130.

Milk flow rate sensor apparatus 200 includes mechanical stops 215, which may also be referred to as steps, which provide visual and tactile feedback that milk flow rate sensor apparatus 200 is correctly installed on manifold base 130. Further, stops 215 may provide a gasket, O-ring, or some other sealing device to ensure that milk flow rate sensor apparatus 200 mates with manifold base 130 in an airtight and liquid tight fashion in order to maintain vacuum pressure within, for example, breast pump 100, shown in FIG. 1.

Internally, milk flow rate sensor apparatus 200 includes a milk draining portion 220 which collects and funnels milk to drain 225 essentially acting as a funnel for milk draining from manifold 115, shown in FIG. 1. Drain 225 serves three functions. First, drain 225 minimizes milk splashing as milk drains from manifold 115 into milk flow rate sensor apparatus 200. Second, drain 225 adjusts the speed of the stream of milk into a controlled and uniform speed. This speed adjustment is facilitated by allowing the milk to pool within milk draining portion 220 and slowly work its way into drain 225. Third, drain 225 reduces bubble formation within milk collected in milk draining portion 220. Since air bubbles are substantially less dense than milk, air bubbles have a tendency to ride on the top of the milk in milk draining portion 220 while droplets of substantially bubble free milk are able to be formed, underneath the bubbles, into drop forming portion 230. Drop forming portion 230 includes a uniform cylindrical opening beginning at drain 225 and extending down to spout 235. Drop forming portion 230 allows milk to drop into the cylinder of drop forming portion 230 at a measureable volume and rate. As the milk enters spout 235, milk is metered into uniform droplets by gravity forming a drop of a particular size based on the surface tension of milk (as the drop volume increases, the surface tension of the milk droplet increases until the drop can no longer remain connected by surface tension to milk within drop forming portion 230 of milk flow rate sensor apparatus 200). A uniform drop of known volume and that is substantially bubble free is thereby created by allowing milk to drip drop by drop through spout 235. Spout 235 may be configured to drip a drop of milk of a predetermined size depending on the diameter of the cylinder of drop forming portion 230. In general, uniform droplets set at a size ranging between 3 mm and 6 mm in diameter are preferable. That is to say each droplet will be consistently the same diameter and that diameter will be between 3 mm and 6 mm in preferable implementations. The outer diameter of the spout region will be between 3 mm and 6 mm in preferable implementations. The center of the field of view of EMR based sensor may be configured to be located a distance at least two times the drop diameter away, below the spout region.

Finally, milk flow rate sensor apparatus 200 includes a sensor 240. It is to be noted that sensor 240 is shown as being disposed at a bottom edge of spout 235 in FIG. 2. However, sensor 240 may be disposed anywhere below spout 235 in milk flow rate sensor apparatus 200 such that sensor 240 may detect droplets of milk using the techniques described herein. For example, sensor 240 may be disposed approximately 2 drop diameter lengths below the drop forming spout or lower (e.g., since droplets have a diameter of between 3 mm and 6 mm, two drop diameter lengths is approximately 6 mm to 12 mm). While sensor 240 will be discussed in more detail below, sensor 240, in general, detects each uniform droplet produced from spout 235 and communicates that information to the one or more processors contained within manifold 115 shown in, for example, FIG. 1. The one or more processors contained within manifold 115, for example, may count the number of droplets and multiply the number of droplets by the volume of each droplet. Since each droplet is substantially uniform, the processor can output a total volume of milk that has been expressed. Further, the processor can determine a total output of milk over a particular amount of time, providing an overall flow rate. It should also be noted that in the case where two different breast pumps are being used simultaneously, processors in one, or both of the breast pumps may communicate with each other or an external device such as a mobile phone, for example. The external device may perform the calculations or just receive calculated information from the one or more processors within manifold 115 of each breast pump. In either case, flow rate and/or volume information may be provided to the user on a per-breast basis. In other words, a user may obtain flow rate and total volume information for a right breast and a left breast individually. In addition, the user may further obtain an overall flow rate and total volume of milk expressed via, for example, the mobile phone. Thus, the user will be provided with information about the volume of milk expressed in each individual bottle and the overall quantity of milk that has been expressed during a particular pump session. Finally, and in another embodiment, the mobile phone may track flow rate and total volume over time (on a per-breast basis or an overall total basis) between pumping sessions such that a user may compare one pumping session to an overall average or another pumping session or series of pumping sessions at a certain time of day.

Figure 3:
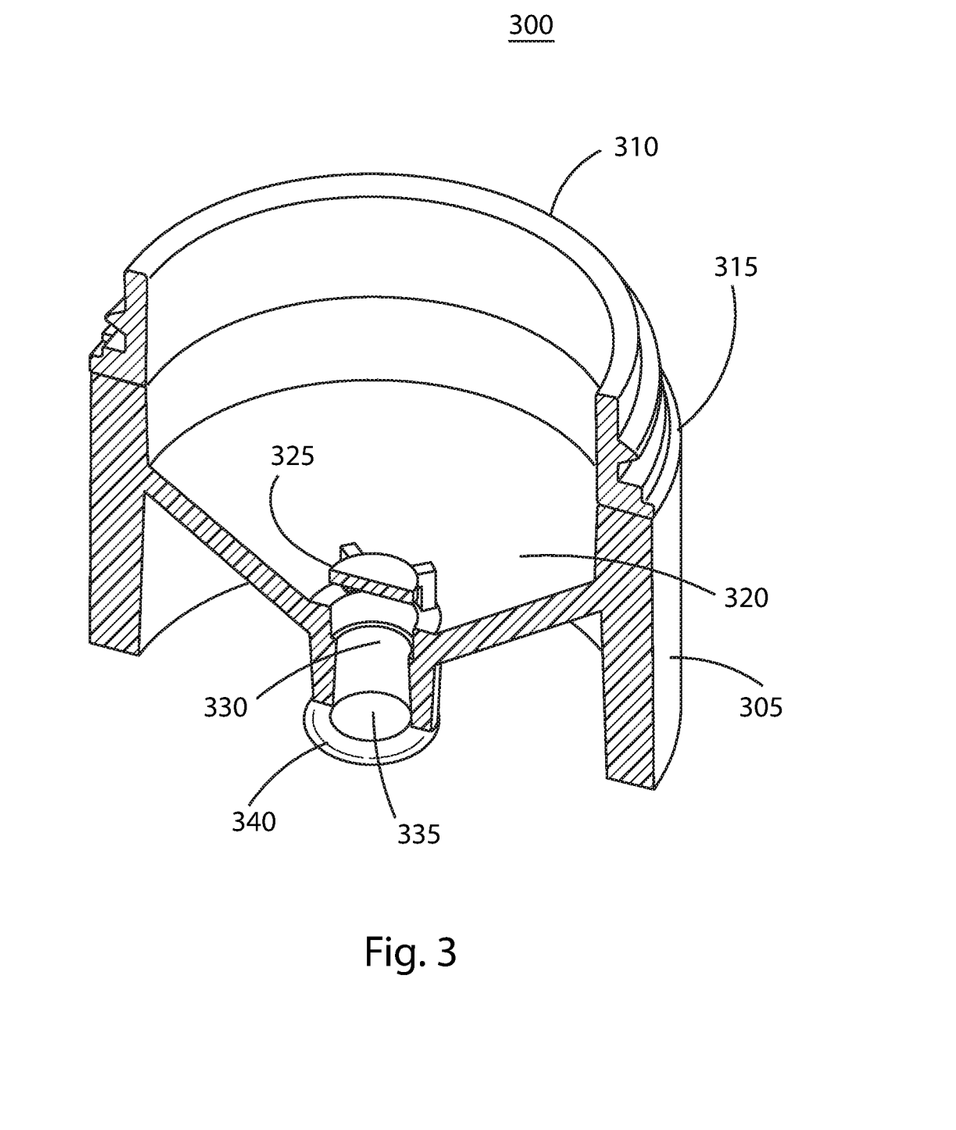
FIG. 3 illustrates an elevated cut-away side perspective of the milk flow rate sensor system and apparatus.

FIG. 3 illustrates an elevated cut-away side perspective of milk flow rate sensor system 300. Milk flow rate sensor system 300 includes a housing 305 and a milk flow rate sensor 340.

Housing 305 may be constructed using an injection molding process to create a hard plastic apparatus and includes several elements, such as connector 310, one or more mechanical stops 315, milk draining portion 320, drain 325, and spout 335. Other materials or methods for making housing 305 include blow molding, injection molding, casting or forging of plastic, glass, metal, or composite materials. Connector 310 is similar in implementation and description to connector 210 shown in FIG. 2. Connector 310 connects housing 305 to, for example, manifold base 130 shown in FIG. 1. Connector 310 may include male mechanical threads which may be connected to manifold base 130 by screwing mechanical threads on connector 310 into female threads on manifold base 130. In one embodiment, connector 310 may implement a "quarter turn lock" mechanical thread engagement system. In this embodiment, housing 305 may be attached to manifold base 130 by turning housing 305 90° into manifold base 130 to form a secure connection housing 305 and manifold base 130.

One or more mechanical stops 315, which may also be referred to as steps, provide visual and tactile feedback that indicate housing 305 is correctly installed on manifold base 130. Further, one or more mechanical stops 315 may provide a gasket, O-ring, or some other sealing device to ensure that housing 305 mates with manifold base 130 in an airtight fashion in order to maintain vacuum pressure within, for example, breast pump 100, shown in FIG. 1.

Milk draining portion 320 collects and funnels milk to drain 325, essentially acting as a funnel for milk draining from manifold 115, shown in FIG. 1. Drain 325 serves three functions. First, drain 325 minimizes milk splashing as milk drains from manifold 115 into housing 305. Second, drain 325 adjusts the speed of the stream of milk into a controlled and uniform speed. This speed is adjustment is facilitated by allowing the milk to pool within milk draining portion 320 and pour in a controlled way into drain 325. Third, drain 325 reduces bubble formation within milk collected in milk draining portion 320. Since air bubbles are substantially less dense than milk, air bubbles have a tendency to ride on the top of the milk in milk draining portion 320 while droplets of substantially bubble free milk are able to be formed, underneath the bubbles, into drop forming portion 330. Drop forming portion 330 includes a uniform cylindrical opening beginning at drain 325 and extending down to spout 335. Drop forming portion 330 allows milk to drop into the cylinder of drop forming portion 330 at a known volume and rate. As the milk enters spout 335, milk is metered into uniform droplets by gravity forming a drop of a particular size based on the surface tension of milk (as the drop volume increases, the surface tension of the milk droplet increases until the drop can no longer remain connected by surface tension to milk within drop forming portion 330 of housing 305). A uniform drop of known volume and that is substantially bubble free is thereby created by allowing milk to drip drop by drop through spout 335.

Finally, milk flow rate sensor system 300 includes a sensor 340. While sensor 340 will be discussed in more detail below, sensor 340, in general, detects each uniform droplet produced from spout 335 and communicates that information to the one or more processors contained within manifold 115 shown in, for example, FIG. 1. It is to be noted that sensor 340 is shown as being disposed at a bottom edge of spout 335 in FIG. 3. However, sensor 340 may be disposed anywhere below spout 335 in milk sensor system 300 such that sensor 340 may detect droplets of milk using the techniques described herein. For example, sensor 340 may be disposed approximately 2 drop diameter lengths below the drop forming spout or lower (e.g., since droplets have a diameter of between 3 mm and 6 mm, two drop diameter lengths is approximately 6 mm to 12 mm). The one or more processors contained within manifold 115, for example, may count the number of droplets and multiply the number of droplets by the volume of each droplet using the adaptable and adjustable multipliers discussed above. Since each droplet is substantially uniform, the processor can output a total volume of milk that has been expressed. Further, the processor can determine a total output of milk over a particular amount of time, providing an overall flow rate. It should also be noted that in the case where two different breast pumps are being used simultaneously, processors in one, or both of the breast pumps may communicate with each other or an external device such as a mobile phone, for example. The external device may perform the calculations or just receive calculated information from the one or more processors within manifold 115 of each breast pump. In either case, flow rate and/or volume information may be provided to the user on a per-breast basis. In other words, a user may obtain flow rate and total volume information for a right breast and a left breast individually. In addition, the user may further obtain an overall flow rate and total volume of milk expressed via, for example, the mobile phone. Thus, the user will know the volume of milk expressed in each individual bottle and the overall quantity of milk that has been expressed during a particular pump session. Finally, and in another embodiment, the mobile phone may track flow rate and total volume over time (on a per-breast basis or an overall total basis) between pumping sessions such that a user may compare one pumping session to an overall average or another pumping session or series of pumping sessions at a certain time of day.

Figure 4:
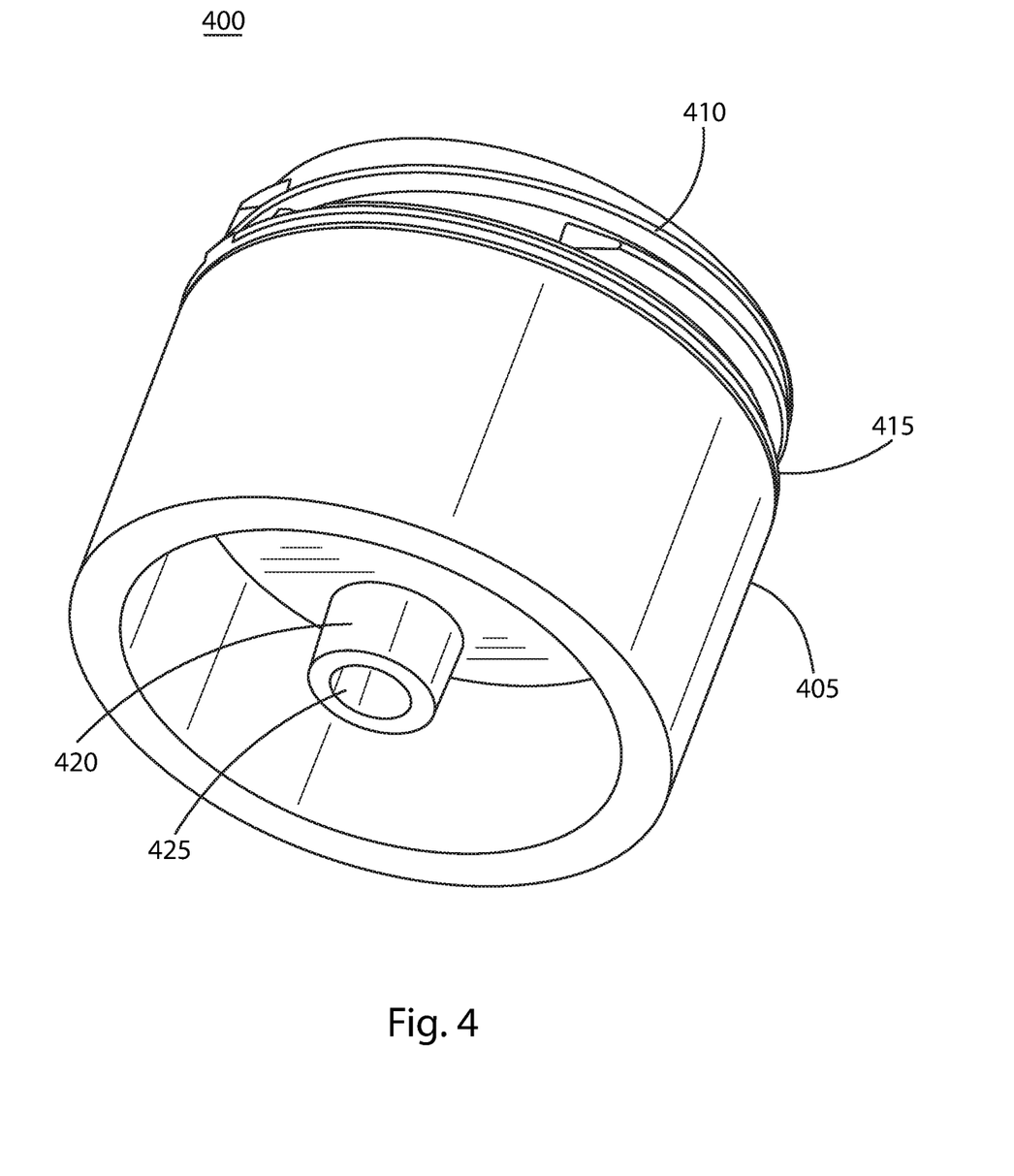
FIG. 4 illustrates bottom side perspective view of the milk flow rate sensor system and apparatus.

FIG. 4 illustrates bottom side perspective view of the milk flow rate sensor apparatus 400, which is similar in implementation and description to milk flow rate sensor apparatus 200, shown in FIG. 2. Milk flow rate sensor apparatus 200 includes housing 405 which may be constructed using an injection molding process to create a hard plastic apparatus. In one embodiment, milk flow rate sensor apparatus 400 includes a connector 410 to connect milk flow rate sensor apparatus 400 to, for example, manifold base 130 shown in FIG. 1. Connector 410 may include male mechanical threads which may be connected to manifold base 130 by screwing mechanical threads on connector 410 into female threads on manifold base 130. In one embodiment, connector 410 may implement a "quarter turn lock" mechanical thread engagement system. In this embodiment, milk flow rate sensor apparatus 400 may be attached to manifold base 130 by turning milk flow rate sensor apparatus 400 90° into manifold base 130 to form a secure connection between milk flow rate sensor apparatus 400 and manifold base 130.

Milk flow rate sensor apparatus 400 includes mechanical stops 415, which may also be referred to as steps, which provide visual and tactile feedback that milk flow rate sensor apparatus 400 is correctly installed on manifold base 130. Further, stops 415 may provide a gasket, O-ring, or some other sealing device to ensure that milk flow rate sensor apparatus 400 mates with manifold base 130 in an airtight fashion in order to maintain vacuum pressure within, for example, breast pump 100, shown in FIG. 1. Other configurations are possible, including mounting milk flow rate sensor apparatus within milk collection apparatus 145, or in manifold 115, shown in FIG. 1, for example.

Milk flow rate sensor apparatus 400 further includes drop forming portion 420 which is implemented as a uniform cylinder extending down to spout 425. Drop forming portion 420 allows milk to drop into the cylinder at a known volume and rate. As the milk enters spout 425, milk is metered into uniform droplets by gravity forming a drop of a particular size based on the surface tension of milk (as the drop volume increases, the surface tension of the milk droplet increases until the drop can no longer remain connected by surface tension to milk within drop forming portion 420 of milk flow rate sensor apparatus 400). A uniform drop of known volume and that is substantially bubble free is thereby created by allowing milk to drip drop by drop through spout 425. It should also be noted that the drop forming portion 420, spout 425, and sensor lens features may be built into and incorporated into manifold 115 and neck of manifold 115 as a single piece to the user, as opposed to a piece that attaches separately.

Milk flow rate sensor apparatus 400 is robust to the user tilting or swaying, as the controlled milk dropper directs drops within range of the sensor. Because the path of the milk droplet could change as the user tilts, sways, reclines, or otherwise moves, the milk flow sensor apparatus 400 is configured to count droplets regardless of where the milk droplet falls from manifold base 130.

Figure 5:
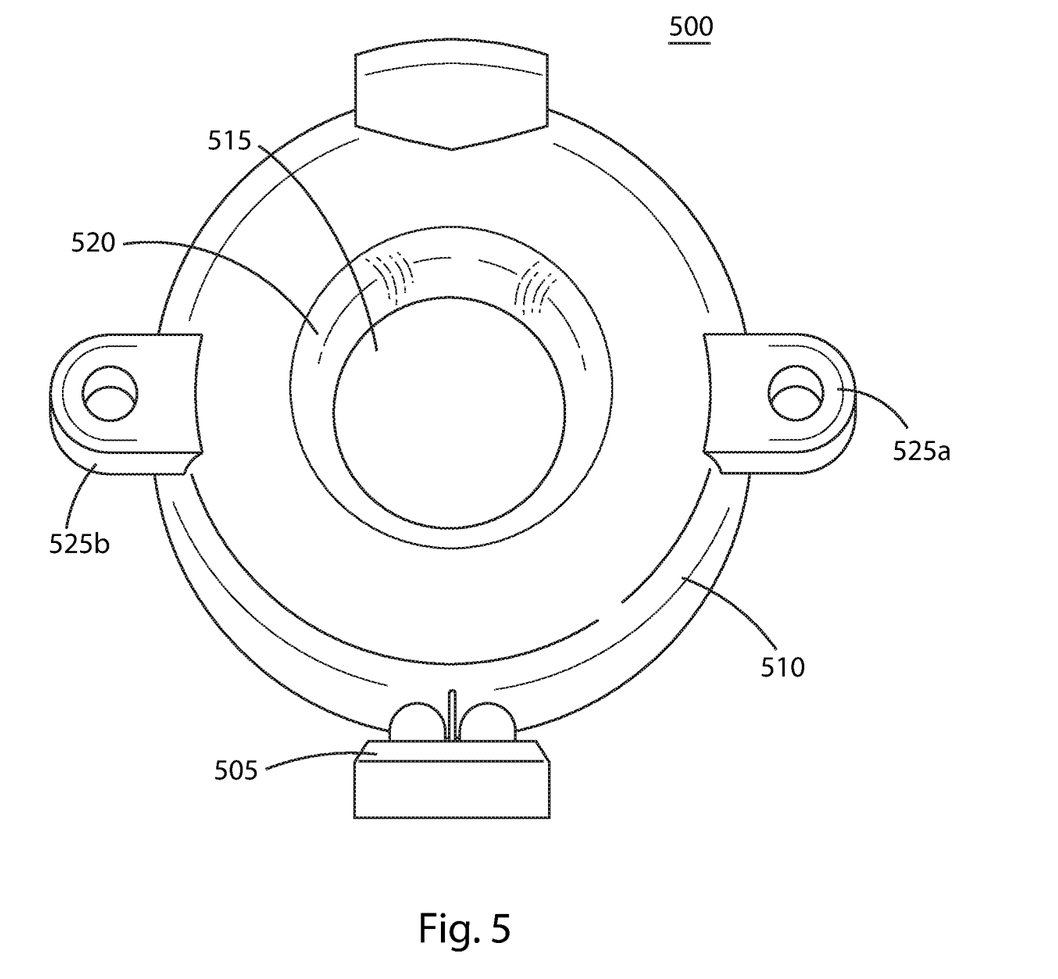
FIG. 5 illustrates a toroidal sensor lens system.

FIG. 5 illustrates a toroidal sensor lens system 500. Toroidal sensor lens system 500 includes an emitter/detector 505. Emitter/detector 505 may be an EMR (electromagnetic radiation) emitter/detector or may be an optical emitter/detector. In practice, emitter/detector 505 emits an electromagnetic radiation pulse and detects the reflected radiation pulse. One drawback of certain emitter/detectors 505 is that their usable range can be inadequate for a particular purpose.

In order to expand the range of emitter/detector 505 and to increase the focus of emitter/detector 505, a toroidal lens 510 is used in concert with emitter/detector 505. Toroidal lens 510 is generally shaped as a toroid as the angles of reflection associated with a toroid are suitable for accurately reflecting a radiation pulse. Further, toroidal lens 510 is particularly suitable for use with emitter/detector 505 because toroidal lens 510 includes a void 515 in the middle which allows milk droplets to pass through and be detected without altering the path of the milk droplet.

In one embodiment, toroidal lens 510 may include a reflective material 520 positioned around void 515 to better reflect radiation pulses emitted from emitter/detector 505. As radiation is emitted from emitter/detector 505, the radiation impacts milk drops falling through void 515. Emitter/Detector 505 interprets any substantial variance in the radiation pulse as detecting a drop of milk. Thus, in order to ensure the radiation pulse is reflected back to emitter/detector 505 without substantial variance, reflective material 520 is positioned around toroidal lens 510 and in void 515 in a manner that ensures that the radiation pulse has no substantial variance and does not detect a droplet that did not fall through void 515. In one embodiment, toroidal lens 510 may include tabs 525a and 525b for attaching toroidal lens 510 to, for example, the bottom of milk flow rate sensor apparatus 400, shown in FIG. 4, for example. However, toroidal lens 510 may also be attached to the bottom of milk flow rate sensor apparatus 400 mechanically by plastic welding or co-molding. In other words, toroidal lens 510 may, but need not be, a discrete part or may be attached or formed with other elements of milk flow rate sensor apparatus 400, shown in FIG. 4, or manifold 115, shown in FIG. 1.

Figure 6:
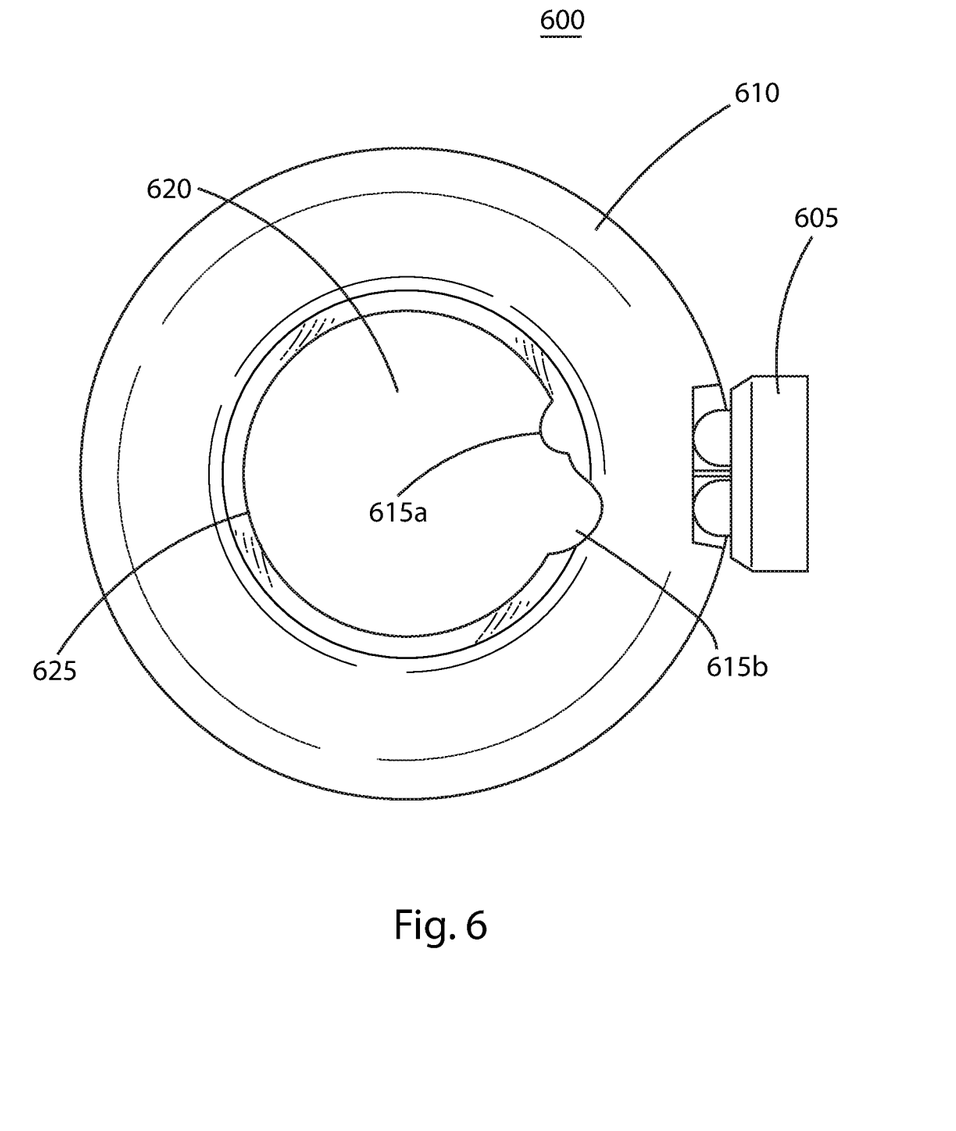
FIG. 6 illustrates a substantially flat circular sensor lens system.

FIG. 6 illustrates substantially flat circular sensor lens system 600. Flat circular sensor system 600 includes an emitter/detector 605. Emitter/detector 605 may be an EMR (electromagnetic radiation) emitter/detector or may be an optical emitter/detector. In practice, emitter/detector 605 emits an electromagnetic radiation pulse and detects the reflected radiation pulse. One drawback of certain emitter/detectors 605 is that their usable range can be inadequate for a particular purpose.

In order to expand the range of emitter/detector 605 and to increase the focus of emitter/detector 605, a substantially flat circular lens 610 is used in concert with emitter/detector 605. Flat circular lens 610 is generally shaped as substantially circular as the angles of reflection associated with a circle are suitable for accurately reflecting a radiation pulse. In one embodiment, flat circular lens 610 may be less than a centimeter in width and three centimeters in outer diameter and considered substantially flat. Further, flat circular lens 610 is particularly suitable for use with emitter/detector 605 because toroidal lens 610 has a void 620 in the middle which allows milk droplets to pass through and be detected without altering the path of the milk droplet. Void 620 may or may not be circular or may be substantially circular with certain convex portions 615a or concave portions 615b about void 620. Convex portions 615a and concave portions 615b may further focus or extend the range of an emitter side of emitter detector 605 or enhance the detection of a reflected electromagnetic pulse. Any number of convex portions 615a and concave portions 615b may be implemented in void 620. Further, only a single convex portion 615a or a single concave portion 615b may be implemented as necessary for any particular desired implementation. Similarly, circular lens 610 may also be attached to the bottom of milk flow rate sensor apparatus 400 mechanically by plastic welding or co-molding. In other words, toroidal lens 610 may, but need not be, a discrete part or may be attached or formed with other elements of milk flow rate sensor apparatus 400, shown in FIG. 4, or manifold 115, shown in FIG. 1.

In one embodiment, flat circular lens 610 may include a reflective material 625 positioned around the surface of void 620 to better reflect radiation pulses emitted from emitter/detector 605. As radiation is emitted from emitter/detector 605, the radiation impacts milk drops falling through void 620. Emitter/Detector 505 interprets any substantial variance in the radiation pulse as detecting a drop of milk. Thus, in order to ensure the radiation pulse is reflected back to emitter/detector 605 without substantial variance, reflective material 625 is positioned around flat circular lens 610 and in void 620 in a manner that ensures that the radiation pulse has no substantial variance and does not detect a droplet that did not fall through void 620.

It is also noted that other shapes for lenses may be implemented toroidal sensor lens system 500 shown in FIG. 5 or flat circular sensor system 600, shown in FIG. 6. Other lenses that may be used may have properties that are similar to those disclosed herein, namely, internal angles conducive for reflecting electromagnetic radiation and allowing milk to pass through a void without adversely affecting the path of the milk. Emitter/detector 505 and emitter detector 605 may operate in the 900-990 nm wavelength range to facilitate detection of milk droplets. Emitter/detector may be in encased in an enclosure which includes a cover made of a material to transmit EMR at the specified operating range. The cover may be opaque to the naked eye.

The sensor range (field of view, FOV) may be improved by providing reflective walls around an outside of the lenses, or otherwise within the breast pump system. Reflective walls above, below, and/or around the sensor may be used with or without any additional lens 510/610. Electromagnetic radiation may be reflected off a reflective surface one or multiple times, on the outside of the lenses or in the breast pump system and may, therefore, experience less loss per unit of energy emitted and therefore improve sensor range. Another improvement to sensor range may be accomplished by illuminating an area around the detectors such that a emitter/detector 505/605 sense reduced light (occluded by a falling droplet) as a drop passes across the emitter/detector.

The foregoing description has been presented for purposes of illustration. It is not exhaustive and does not limit the invention to the precise forms or embodiments disclosed. Modifications and adaptations will be apparent to those skilled in the art from consideration of the specification and practice of the disclosed embodiments. For example, components described herein may be removed and other components added without departing from the scope or spirit of the embodiments disclosed herein or the appended claims.

Other embodiments will be apparent to those skilled in the art from consideration of the specification and practice of the disclosure disclosed herein. It is intended that the specification and examples be considered as exemplary only, with a true scope and spirit of the invention being indicated by the following claims.

What is claimed is:

1. A breast pump, comprising:
    a manifold;
    a drain including a connector which allows the drain to connect to the manifold or disconnect from the manifold, the drain including a droplet forming spout;
    a sensor disposed under the droplet forming spout, wherein the sensor detects droplets of milk released from the spout.

2. The breast pump of claim 1, further comprising a flange connectable to the manifold, wherein a sensor is disposed in the manifold.

3. The breast pump of claim 1, further comprising a valve disposed below the drain, wherein the sensor is disposed between the manifold and the valve in the breast pump.

4. The breast pump of claim 1, further comprising a valve disposed below the drain, wherein the sensor is disposed below the valve in the breast pump.

5. The breast pump of claim 1, wherein the manifold includes a flexible portion and, wherein a sensor is disposed at the flexible portion of the manifold.

6. The breast pump of claim 1, further comprising one or more processors receiving sensor data from the sensor.

7. The breast pump of claim 6, wherein one of the one or more processors is disposed in one of the manifold, a collection container, and a mobile device.

8. The breast pump of claim 1, wherein the spout forms droplets with a diameter between 3 millimeters and 6 millimeters.

9. The breast pump of claim 1, wherein the sensor is disposed at least two droplet diameter lengths below the spout.

10. The breast pump of claim 1, wherein sensor data is transmitted to a mobile device.

11. The breast pump of claim 1, further comprising a lens, wherein the lens is toroidal.

12. The breast pump of claim 11, wherein an outside surface of the toroidal lens is reflective.

13. The breast pump of claim 1, further comprising a lens, wherein the lens is circular.

14. A breast pump, comprising:
    a drain apparatus, connectable to a manifold, and including a droplet forming spout;
    a sensor, connectable to the drain apparatus, and disposed under the droplet forming spout, wherein the sensor detects droplets of milk released from the spout.

15. The breast pump of claim 14, wherein the breast pump further includes a valve and a collection apparatus and wherein the valve connects to the collection apparatus.

16. The breast pump of claim 15, wherein the collection apparatus connects to the manifold such that the drain apparatus, the sensor, and the valve are disposed within the breast pump.

17. The breast pump of claim 16, wherein the manifold further connects to a flange.

18. The breast pump of claim 17, wherein the manifold includes a tubing adapter.

19. The breast pump of claim 18, further comprising a lens associated with the sensor, wherein the lens is one of a circular lens and a toroidal lens.

* * * * *